United States Patent [19]
Nagasaki

[11] Patent Number: 4,907,573
[45] Date of Patent: Mar. 13, 1990

[54] ULTRASONIC LITHOTRESIS APPARATUS

[75] Inventor: Tatsuo Nagasaki, Yokohama, Japan

[73] Assignee: Olympus Optical Co., Ltd., Tokyo, Japan

[21] Appl. No.: 167,356

[22] Filed: Mar. 14, 1988

[30] Foreign Application Priority Data

Mar. 21, 1987 [JP] Japan .................................. 62-67519
Apr. 17, 1987 [JP] Japan .................................. 62-94973

[51] Int. Cl.⁴ ............................................ A61B 17/22
[52] U.S. Cl. .................................. 128/24 A; 310/320; 310/334; 367/155
[58] Field of Search ................. 128/24 A, 328, 660.03, 128/662.03, 660.01; 604/22; 73/625, 628, 642; 310/320, 334–336; 367/153, 155

[56] References Cited

U.S. PATENT DOCUMENTS

| | | | |
|---|---|---|---|
| 2,779,191 | 1/1957 | Willard | 310/334 |
| 3,569,750 | 3/1971 | Beaver | 310/320 |
| 4,276,491 | 6/1981 | Daniel | 128/662.03 X |
| 4,485,321 | 11/1984 | Klicker et al. | 310/320 X |
| 4,547,748 | 10/1985 | Ballato | 310/320 X |
| 4,635,484 | 1/1987 | Lerch | 128/662.03 X |
| 4,658,828 | 4/1987 | Dory | |

Primary Examiner—Ruth S. Smith
Attorney, Agent, or Firm—Frishauf, Holtz, Goodman & Woodward

[57] ABSTRACT

A large number of piezoelectric elements are arranged in a mosaic pattern on a spherical surface so that ultrasonic waves generated by the elements converge on a single point. The arrangement of the elements constitutes a transducer. With the transducer applied to a subject through a liquid bag filled with water, ultrasonic shock waves from each piezoelectric element are concentrated on a lithotresis object, or a calculus so as to break it. The ultrasonic shock waves are generated by applying driving impulses (voltage) to each piezoelectric element. In order to locate the calculus, the transducer is coupled to an ultrasonic diagnosis apparatus having a mechanical scanning type ultrasonic probe. The piezoelectric elements have resonance frequencies set such that the piezoelectric element positioned at the center of the transducer has the lowest resonance frequency and the resonance frequency of each piezoelectric element is increased in accordance with its distance from the center. Thus, the frequency range of vibration of the transducer is broadened so that the ultrasonic shock waves become low in negative sound pressure and narrow in pulse width at the point of convergence.

5 Claims, 6 Drawing Sheets

ULTRASONIC LITHOTRESIS APPARATUS

BACKGROUND OF THE INVENTION

1. Field of the Invention

This invention relates to an ultrasonic lithotresis apparatus for directing ultrasonic shock waves from the outside of a body to a diseased portion in the body, and treating the diseased portion, for example, by breaking a renal calculus or kidney stone.

2. Description of the Related Art

As prior art there are known an ultrasonic pulse apparatus for breaking renal calculi disclosed in Japanese laid-open patent application No. 60-145131, and an apparatus for examining and locating tumors using ultrasound disclosed in U.S. Pat. No. 4,658,828.

In these apparatus a large number of piezoelectric elements are arranged in a mosaic pattern on a spherical surface, thus constituting a transducer assembly. With the transducer applied to a subject (patient) through a liquid bag filled with an ultrasonic medium such as water, ultrasonic shock waves are transmitted by the piezoelectric elements so as to concentrate or converge on a diseased portion in the kidney, namely, a calculus, thereby breaking the calculus.

The ultrasonic shock waves are generated by applying a driving impulse voltage to each of the piezoelectric elements from a driving circuit.

In order to locate the calculus a mechanical scanning type ultrasonic probe is mounted on the transducer assembly. An ultrasonic diagnosis apparatus is coupled to the probe.

Figure 1:
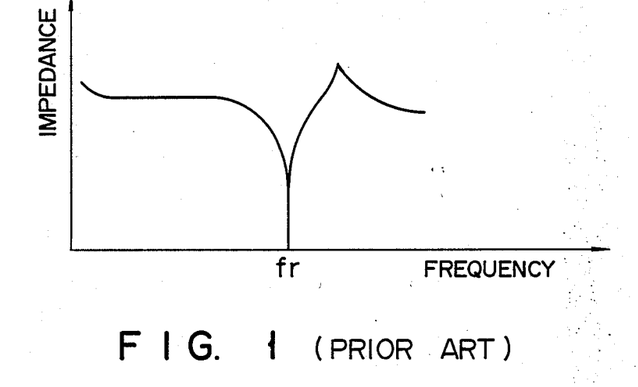
FIG. 1 shows impedance characteristics of an ordinary piezoelectric element.

In view of conversion efficiency the piezoelectric element is formed of an inorganic piezoelectric material such as lead zirconate titanate (PZT) or an organic high polymer piezoelectric material such as PVDF. The piezoelectric element is usually driven at its resonance frequency because of its impedance characteristics. The impedance characteristics are as shown in FIG. 1.

Figure 2:
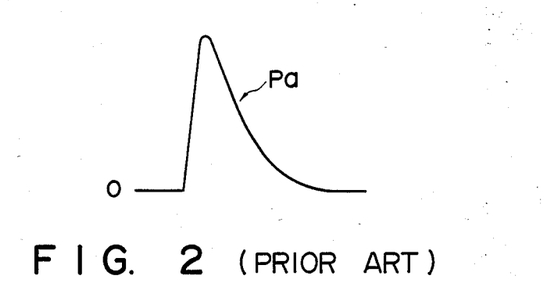
FIG. 2 shows the waveform of a drive signal for the ordinary piezoelectric element.
Figure 3:
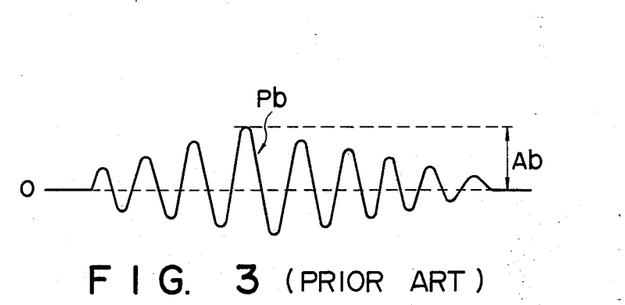
FIG. 3 shows the waveform of an ultrasonic shock wave generated by the drive signal shown in FIG. 2.

As shown, the piezoelectric element has a considerably high impedance at the frequency range without the resonance frequency. The piezoelectric element has a low impedance and high Q at the resonance frequency. The piezoelectric element vibrates in a very narrow bandwidth centered at the resonance frequency fr. Thus, even if a driving impulse voltage as shown in FIG. 2 is applied to an element, an ultrasonic shock wave generated by the element exhibits a waveform Pb which vibrates positive and negative with respect to a sound pressure level of 0 as shown in FIG. 3. This means that negative amplitude, i.e. negative sound pressure is generated. The negative sound pressure creates vacuum bubbles in the body fluid. Since the surrounding tissues contract as the bubbles disappear, there is the possibility of destroying the living tissues. This phenomenon is generally called "cavitation."

The vibrational waveform Pb does not coincide with the driving pulse waveform Pa.

The frequency spectrum of the vibrational waveform Pb is near to the mono-spectrum consisting of a single frequency component, and its amplitude (peak sound pressure) Ab becomes small as compared with driving pulse Pa. Thus, energy of the ultrasonic shock wave becomes small as well. Further, the vacuum bubbles created by the negative sound pressure absorb the energy. As a result, the ultrasonic shock waves will be attenuated before reaching an object such as the calculus, thus causing the possibility of insufficient break of the calculus.

Accordingly, it is proposed that a damping material is laminated on the rear side of the transducer in order to make the Q of the transducer extremely small and thus broaden the frequency range (bandwidth) of vibration. Owing to the damping material a shock wave can be generated which is almost similar in waveform to the driving waveform and wherein has small negative sound pressure On the other hand, however, the damping material adversely affects the conversion efficiency.

Further, it is proposed that the transducer is driven at a frequency in a frequency range below the resonance frequency that is flat in the impedance characteristics so as to realize a vibrational waveform close to an optimum waveform. However, by the use of the frequency range in which the Q of the transducer is small the conversion efficiency is still poor.

SUMMARY OF THE INVENTION

It is an object of this invention to provide an ultrasonic lithotresis apparatus for preventing the "cavitation" phenomenon, and securely and reliably treating a calculus or malignant tumor (cancer) within the body of a patient.

It is another object to provide an ultrasonic lithotresis apparatus for enabling a piezoelectric element to be used at high conversion efficiency, and raising the sound pressure of ultrasonic shock waves without increasing a driving power for the transducer.

According to an aspect of the present invention there is provided an ultrasonic lithotresis apparatus comprising a transducer having a plurality of piezoelectric elements arranged so that ultrasonic waves generated by the piezoelectric elements converge at a point, and wherein the nearer the center of the transducer, the lower is the resonance frequency of the respective piezoelectric elements; and a driving circuit for applying a driving pulse to each of the piezoelectric elements.

According to another aspect of the present invention there is provided an ultrasonic lithotresis apparatus comprising a transducer; an acoustic dispersion medium mounted on the front side of the transducer and having predetermined frequency dispersion characteristics; and driving means for applying a drive signal to the transducer, the waveform of the driving signal being a chirp waveform frequency modulated in accordance with the frequency dispersion characteristics of the acoustic dispersion medium.

DETAILED DESCRIPTION OF THE PREFERRED EMBODIMENTS

Figure 4:
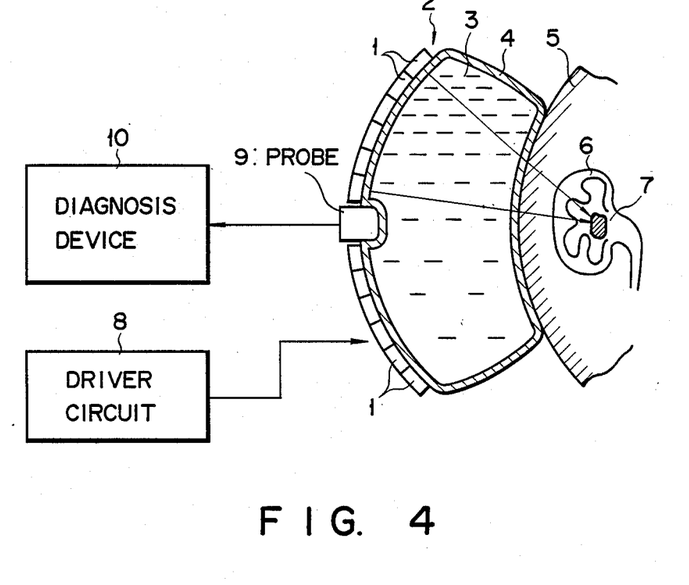
FIG. 4 is a block diagram of an ultrasonic lithotresis apparatus according to a first embodiment of this invention.

Referring now to FIG. 4 a large number of piezoelectric elements 1 are arranged in a mosaic pattern on a spherical surface so that ultrasonic waves transmitted from the elements converge on a single point. The arrangement of piezoelectric elements 1 constitute a transducer 2. With transducer 2 applied to a subject (patient) 5 through a liquid bag 4 filled with an ultrasonic transmission medium 3 such as water, ultrasonic shock waves generated by piezoelectric elements 1 converge on a diseased portion existing in kidney 6, or a calculus 7 to be treated and break it. The water is used as an acoustic transmission medium in order that the ultrasonic shock waves do not attenuate during its propagation.

The ultrasonic shock wave is generated by applying a driving impulse voltage as shown in FIG. 2 to piezoelectric elements 1 from a driving pulse generator 8.

A mechanical-scanning type ultrasonic probe 9 and an ultrasonic diagnosis device 10 coupled to probe 9 are provided for the purpose of locating calculus 7.

In view of conversion efficiency piezoelectric element 1 is formed of an inorganic piezoelectric material such as lead zirconate titanate (PTZ) or an organic high polymer piezoelectric material such as PVDF.

Figure 5:
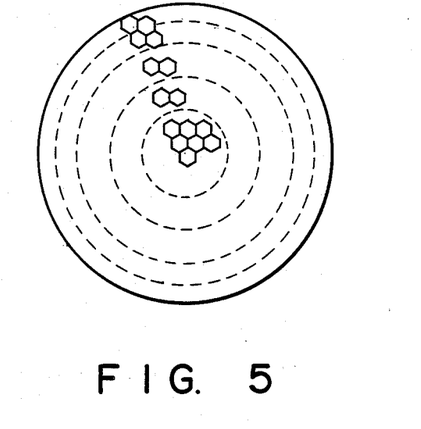
FIG. 5 is a plan view of the transducer used in the first embodiment.

FIG. 5 shows a plan view of transducer 2.

A large number of piezoelectric elements 1 are arranged in a mosaic pattern. It is to be noted here that the resonance-frequency characteristics of transducer 2 are set such that the resonance frequency fr of each of piezoelectric elements 1 is stepwisely increased in accordance with its distance from the center of transducer 2. The concentric rings shown by broken lines in FIG. 5 represent the areas in which the elements 1 have the same resonance frequency. Each ring has the same number of elements 1.

The distribution of sound pressure generated by a pulse energization of transducer 2 about the point of convergence of the ultrasonic shock waves within the subject will be discussed below.

Figure 6:
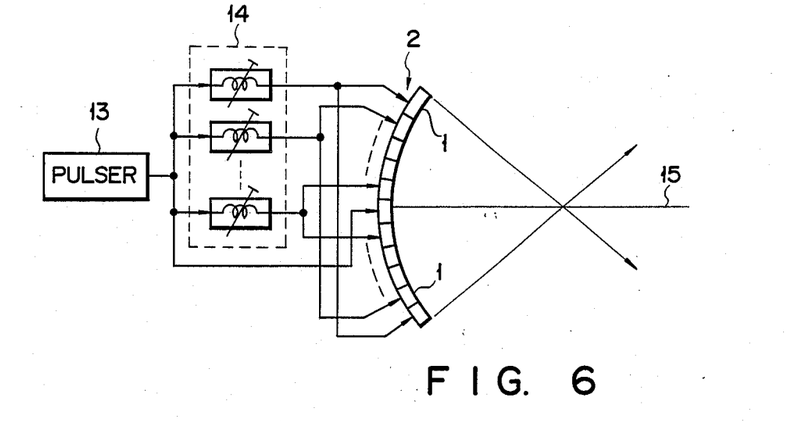
FIG. 6 is a diagram useful for explaining the operation of the first embodiment.

FIG. 6 is a schematic of the first embodiment for considering the distribution of the sound pressure about the point of convergence of the ultrasonic shock waves. For simplification of the description, it is assumed that piezoelectric elements 1 are in onedimensional arrangement. A pulse 13 and delay lines 14 correspond to drive pulse generator 8 of FIG. 4. Delay lines 14 are adapted for finely shifting the phases of the drive pulses from pulser 13 for each piezoelectric element so that the phases of the ultrasonic waves transmitted from piezoelectric elements 1 coincide with each other at the point of convergence.

Figure 7:
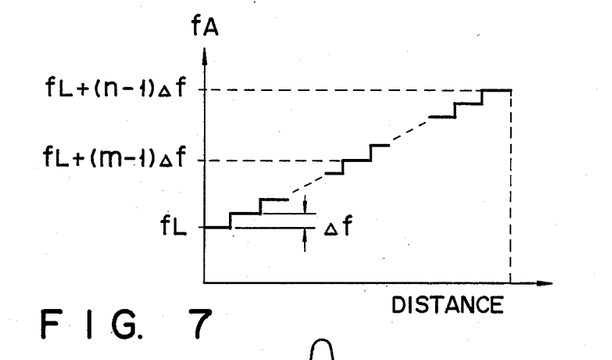
FIG. 7 shows the spatial-frequency component distribution of the ultrasonic wave pulse along the central axis of the transducer.

Since piezoelectric elements 1 have different resonance frequencies, the spatial frequency components fA of the ultrasonic pulses along central axis (x axis) 15 of transducer 2 consist of n stepped components as shown in FIG. 7. Assume here that a parameter m for piezoelectric elements is m=1 for the central piezoelectric element and m=n for the outermost piezoelectric element. Then the sound pressure distribution P(x) along central axis 15, or in the x direction will be expressed as follows:

$$P(x) = \sum_{m=1}^{n} \sin 2\pi (fL + (m - 1)\Delta f)x \quad (1)$$
$$= (\sin n\pi \Delta f x) \div (\sin \pi \Delta f x)$$
$$(\sin 2\pi (fL + (n/2)\Delta f)x$$

where fL stands for the lowest frequency (the spatial frequency of the ultrasonic pulse transmitted from the central piezoelectric element) of the stepwise varying frequencies, and Δf the step size in the frequency variation.

Figure 8:
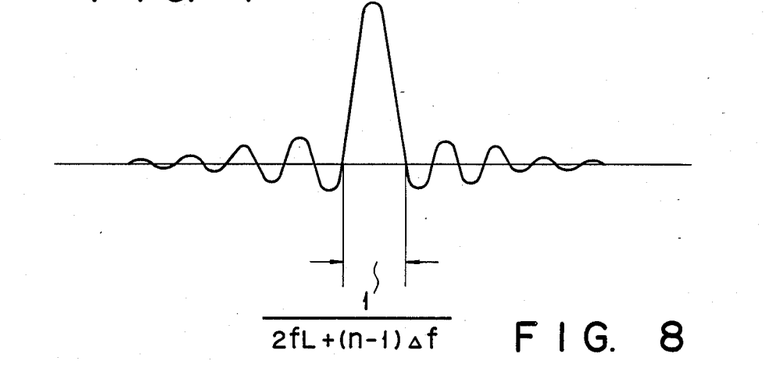
FIG. 8 shows the sound-pressure distribution of the ultrasonic waves about the point of convergence in the direction of the central axis of the transducer.

FIG. 8 shows the distribution P(x) of the sound pressure as found from equation (1). It will be noted from FIG. 8 that the negative pressure is low, the pulse width is relatively small, and the degree of convergence is high.

Figure 9:
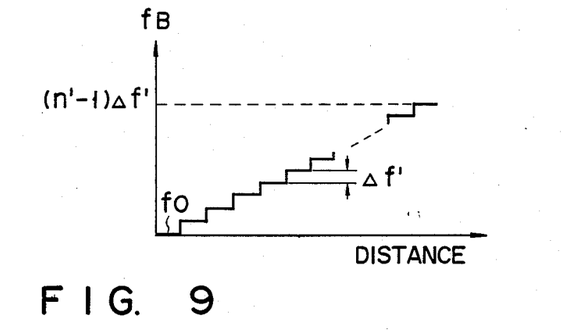
FIG. 9 shows the spatial-frequency component distribution of the ultrasonic wave pulse in a direction orthogonal to the central axis.
Figure 10:
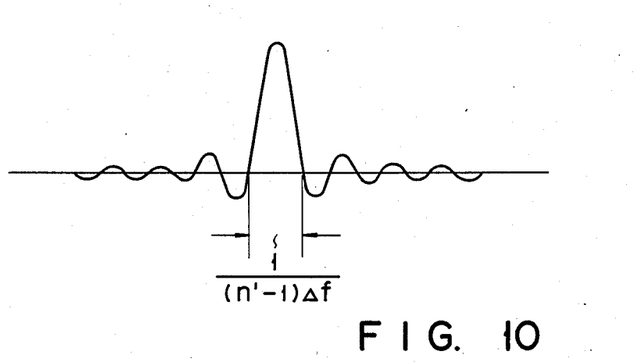
FIG. 10 shows the sound-pressure distribution of the ultrasonic waves about the point of convergence in the direction orthogonal to the central axis.

Next, the distribution of the sound pressure in the direction (azimuthal direction) orthogonal to the central axis 15 will be considered. The spatial frequency components fB of the ultrasonic pulse in the azimuthal direction are approximately represented by stepped components as shown in FIG. 9 as in the case of central axis 15. As shown in FIG. 9 the spatial frequency component f0 of the central piezoelectric element of transducer 2 in the azimuthal direction is 0. Namely, the sound pressure distribution in the azimuthal direction can be obtained by substituting fL=0 into equation (1). This is shown in FIG. 10. As will be evident from FIG. 10 the negative pressure is low, the pulse width is relatively small, and the degree of convergence is high.

According to the first embodiment, as described above, piezoelectric elements of different resonance frequencies are combined into a transducer, and the ultrasonic waves transmitted from these piezoelectric elements converge on a point. Thus, the vibrational frequency range of the piezoelectric elements is broadened. This provides the following advantages. That is, since the ultrasonic shock waves are low in the negative pressure at the point of convergence, the "cavitation"

phenomenon within the subject can be prevented, thus increasing the security of the subject. Further, since the ultrasonic shock waves are small in the pulse width at the point of convergence, the degree of convergence of the ultrasonic shock waves on a diseased portion can be increased. As a result, an exact treatment can be performed and the security for portions other than the diseased portion can be improved. In addition, use may be made of piezoelectric elements of high Q with the result that good conversion efficiency, low power dissipation and simplicity in the construction are achieved.

A modification of the first embodiment will be described. By not only varying the resonance frequency of each piezoelectric element but also varying the amplitude of the drive pulse, the size of each piezoelectric element, or the number of elements 1 included in each ring, the negative pressure of the ultrasonic shock waves can be further lowered. For example, by making the amplitude of low frequency components of the drive pulse which are applied to the central elements larger than that of high frequency components which are applied to the peripheral elements, a vibrational waveform can be obtained in which the negative sound pressure is further suppressed though the pulse width is somewhat widened as shown in FIG. 11.

Figure 11:
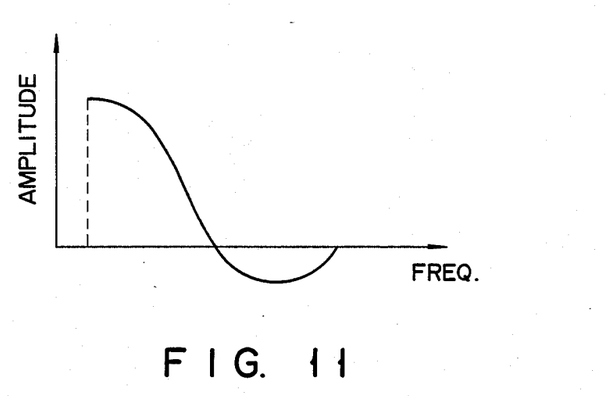
FIG. 11 shows the waveform of a drive pulse, in which an amplitude of the low frequency component is largely modulated than that of the high frequency component, used in a modification of the first embodiment.
Figure 12:
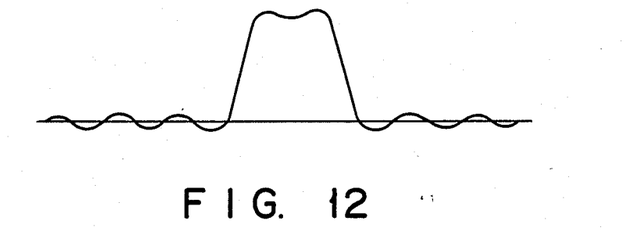
FIG. 12 shows the waveform of the ultrasonic shock wave obtained in the modification.

FIG. 12 shows the distribution of the sound pressure at the focal point when the drive voltage shown in FIG. 11 is applied to the transducer. As compared to the waveform shown in FIGS. 8 and 10, the waveform of FIG. 12 has a lower negative pressure which causes the cavitation, though its pulse width is wider than those of FIGS. 8 and 10 and the degree of convergence is lower than those of FIGS. 8 and 10.

With the embodiments described above, the ultrasonic diagnosis device is used for locating an object to be treated. Alternatively, use may be made of a diagnosis device using X rays. In order for ultrasonic shock waves to converge at a point the piezoelectric elements are spherically arranged. Alternatively, the piezoelectric elements may be arranged flatly. In this case, it is possible to converge the ultrasonic shock waves by the use of a separately disposed ultrasonic lens. It is also possible to converge the ultrasonic shock wave by controlling the delay times for the respective piezoelectric elements.

Figure 13:
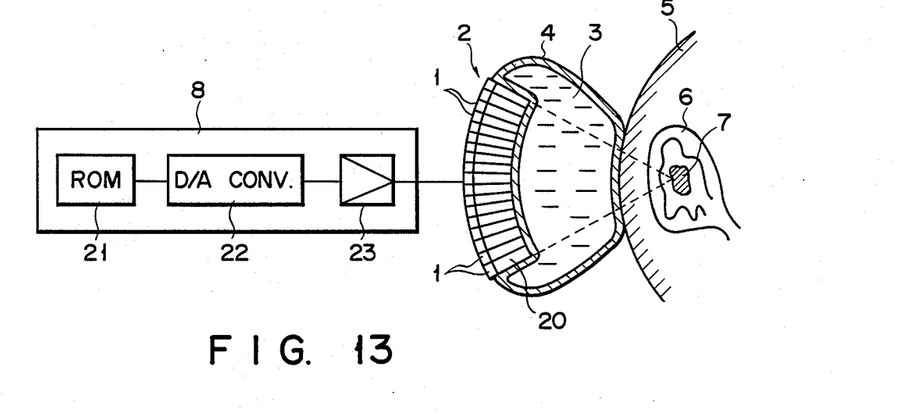
FIG. 13 is a block diagram of the ultrasonic lithotresis apparatus according to a second embodiment of this invention.

FIG. 13 shows a second embodiment of this invention. This embodiment will be described in connection with only the different parts from the first embodiment. Acoustic dispersion mediums 20 are mounted on the front sides of respective piezoelectric elements 1.

Acoustic dispersion mediums 20 are each made of a rod or fiber of crystal or quartz. Acoustic dispersion mediums 20 are each tapered so that they form a spherical surface as the piezoelectric elements form. Acoustic dispersion mediums 20 have such frequency dispersion characteristics that the lower the frequency, the longer is the delay time.

Figure 14:
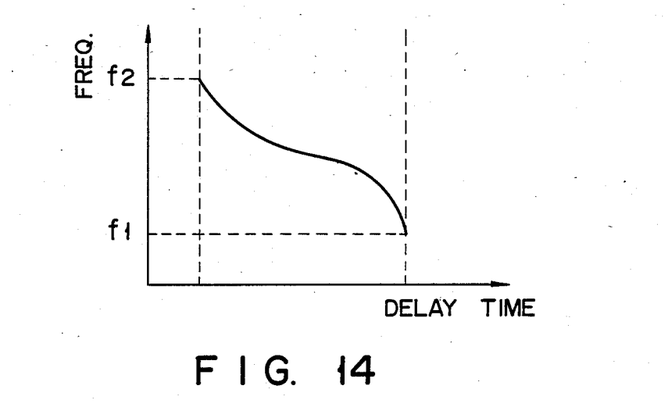
FIG. 14 shows frequency-dispersion characteristics of an acoustic dispersion medium used in the second embodiment.
Figure 15A:
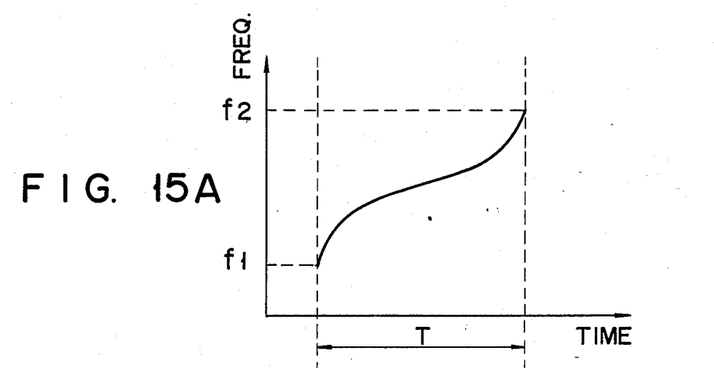
FIG. 15A shows a frequency modulation of a pulse waveform which is frequency-modulated and which is stored in a memory of the second embodiment.
Figure 15B:
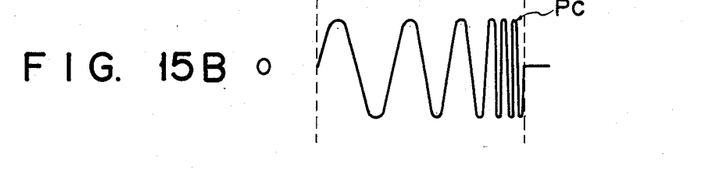
FIG. 15B shows the waveform of a drive signal obtained by the frequency modulation shown in FIG. 15A and used in the second embodiment.

A drive circuit 8 coupled to transducer 2 comprises a read only memory (ROM) 21 for storing a waveform of a drive pulse, a digital to analog (D/A) converter 22 for converting a digital output read out of ROM 21 to an analog signal, and an amplifier 23 for amplifying the analog signal. ROM 21 stores a chirp waveform subjected to frequency modulation as shown in FIG. 15B in accordance with the inverse frequency dispersion characteristics (FIG. 15A) of the frequency dispersion characteristics (FIG. 14) of acoustic dispersion mediums 20. Usually the piezoelectric element is driven by a drive pulse such as shown in FIG. 2 or by a sine wave whose frequency is not varied with the lapse of time. In the second embodiment the piezoelectric element is driven by a chirp wave whose frequency is modulated in accordance with the characteristic shown in FIG. 15A.

Figure 16:
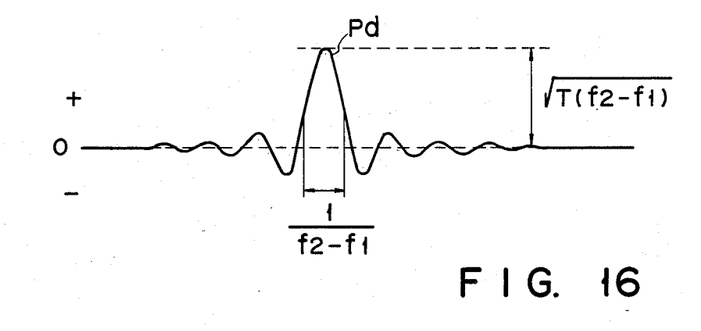
FIG. 16 shows the waveform of an ultrasonic shock wave obtained in the second embodiment.

According to the second embodiment, when a command to generate shock waves is applied to drive circuit 8 the chirp waveform is read out of ROM 21 and then converted by D/A converter 22 to a chirp drive pulse which is in turn applied through amplifier 23 to each of piezoelectric elements 1 of transducer 2. As a result, an ultrasonic shock wave having the chirp waveform as shown in FIG. 15B is generated from piezoelectric element 1 as well. This shock wave is subjected to pulse compression during propagation through acoustic dispersion medium 20 having the frequency dispersion characteristics as shown in FIG. 14. This results in coincidence in the phases of frequency components from f1 to f2 shown in FIG. 15A. An ultrasonic pulse including the various frequency components as shown in FIG. 15B is generated from transducer 2. The various frequency components are superposed (compressed) to result in a waveform as shown in FIG. 16. In other words, this is equivalent to the inverse Fourier transform of the frequency spectral components of f1 to f2 in FIG. 15A. Therefore, the ultrasonic shock waves passing through acoustic dispersion mediums 20, being subjected to the pulse compression, become small in negative sound pressure as shown in FIG. 16. The amplitude of the ultrasonic shock wave (positive peak sound pressure) is $\sqrt{T \times (f2-f1)}$ times as large as that of the drive pulse. The pulse width of the ultrasonic shock wave is $1/(f2-f1)$ which is smaller than the time period T (FIG. 15B). And the ultrasonic shock waves subjected to the pulse compression are concentrated on the calculus 7 through water bag 4 so that the calculus is effectively broken.

As described above, in the second embodiment also, the transducer can be driven in a broad frequency range by the use of the principle of the pulse compression due to the chirp waveform. Thus, the second embodiment provides the same advantage as the first embodiment.

Figure 17:
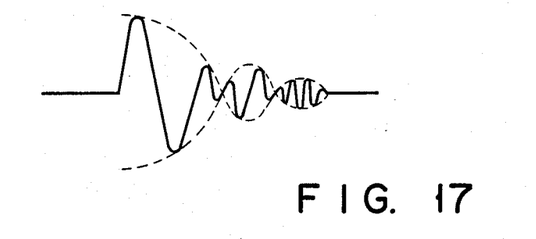
FIG. 17 shows the waveform of a drive signal used in a modification of the second embodiment.

In the case of the second embodiment, a further decrease in the negative pressure will be achieved by making frequency f1 for the chirp waveform stored in ROM 21 as low as possible, or modulating the amplitude of the pulse waveform in accordance with frequency as shown in FIG. 17.

The acoustic dispersion medium is not limited to crystal or quartz. It is required only that the acoustic dispersion medium be a material having frequency dispersion characteristics which subject the frequency-modulated pulse wave (chirp wave) to pulse compression. Thus, amorphous metal or ceramic may be used as well.

What is claimed is:

1. An ultrasonic lithotresis apparatus comprising:
shock wave generating means for generating ultrasonic shock waves and for converging the shock waves on a single point, said shock wave generating means including a plurality of piezoelectric elements arranged in a mosaic pattern, said piezoelectric elements having different resonance frequencies which increase stepwise in accordance with the distance between each piezoelectric element and the center of the piezoelectric elements arranged in said mosaic pattern; and drive means for applying drive pulses to all of said piezoelectric elements of said shock wave generating means.

2. An apparatus according to claim 1, wherein said plurality of piezoelectric elements are arranged in said mosaic pattern on a spherical surface.

3. The apparatus according to claim 2, wherein said drive means comprises:
   means for applying drive pulses having low frequency components to piezoelectric elements positioned at the central portion of said mosaic pattern; and
   means for applying drive pulses having high frequency components to piezoelectric elements positioned at peripheral portions of said mosaic pattern;
   the amplitude of said low frequency components being greater than the amplitude of said high frequency components.

4. The apparatus according to claim 2, wherein said plurality of piezoelectric elements are arranged such that elements of the same resonance frequency are arranged on concentric rings of said mosiac pattern.

5. The apparatus according to claim 1, wherein said drive means comprises:
   means for applying drive pulses having low frequency components to piezoelectric elements positioned at the central portion of said mosaic pattern; and
   means for applying drive pulses having high frequency components to piezoelectric elements positioned at peripheral portions of said mosaic pattern;
   the amplitude of said low frequency components being greater than the amplitude of said high frequency components.

* * * * *